(12) United States Patent
Schwindt et al.

(10) Patent No.: US 11,341,352 B2
(45) Date of Patent: May 24, 2022

(54) METHOD OF ASSESSING A PILOT EMOTIONAL STATE

(71) Applicant: GE Aviation Systems Limited, Cheltenham (GB)

(72) Inventors: Stefan Alexander Schwindt, Cheltenham (GB); Alexander S. Chen, Long Beach, CA (US); Peter H. Tu, Niskayuna, NY (US)

(73) Assignee: GE AVIATION SYSTEMS LIMITED, Cheltenham (GB)

( * ) Notice: Subject to any disclaimer, the term of this patent is extended or adjusted under 35 U.S.C. 154(b) by 24 days.

(21) Appl. No.: 16/702,747

(22) Filed: Dec. 4, 2019

(65) Prior Publication Data

US 2020/0242343 A1    Jul. 30, 2020

(30) Foreign Application Priority Data

Dec. 11, 2018 (GB) .................................... 1820115

(51) Int. Cl.
  *G06K 9/00*     (2022.01)
  *A61B 5/18*     (2006.01)
  *G10L 25/63*    (2013.01)

(52) U.S. Cl.
  CPC ............ *G06K 9/00335* (2013.01); *A61B 5/18* (2013.01); *G10L 25/63* (2013.01)

(58) Field of Classification Search
  CPC ..... A61B 5/0077; A61B 5/1128; A61B 5/165; A61B 5/18; A61B 5/6888; A61B 5/6893;
  (Continued)

(56) References Cited

U.S. PATENT DOCUMENTS 6,799,094 B1  9/2004  Vaida et al.
6,943,700 B2  9/2005  Ceccom et al.
(Continued)

FOREIGN PATENT DOCUMENTS

CN   104751601 A   7/2015
EP    1340995 A1   9/2003
(Continued)

OTHER PUBLICATIONS

Great Britain Office Action Corresponding to Application No. 1820115 dated Jun. 20, 2019.
(Continued)

*Primary Examiner* — Naomi J Small
(74) *Attorney, Agent, or Firm* — Dority & Manning, P.A.

(57) ABSTRACT

A method 140 of assessing an operator emotional state 131 and sending an alert 144 based on the emotional state 131. The method 140 includes tracking 141 during a time period, using at least one sensor 103, 105, 106, 112, 117, one of an image sensor data, voice data or a biometric parameter of an operator. Determining 142, using a controller 120 that is operatively connected to at least one sensor 103, 105, 106, 112, 117, a probability of a likely emotional state 131 from a list of emotional states 131 of an operator based on one of the image sensor data, voice data or the biometric parameter. Comparing 143, using a processor, the probability of one of the likely emotional states 131 of the operator with a baseline emotional state 131 of the operator. Sending 144, using the controller 120, an alert if most likely emotional state deviates from the baseline emotional state by a predetermined threshold.

5 Claims, 6 Drawing Sheets

(58) Field of Classification Search
CPC .............. A61B 5/746; B64D 45/0053; B64D 45/0059; G06K 9/00335; G08B 21/06; G10L 25/63
USPC .......................................................... 382/103
See application file for complete search history.

(56) References Cited

U.S. PATENT DOCUMENTS

| | | | |
|---|---|---|---|
| 7,379,795 | B2 | 5/2008 | Arnouse |
| 7,406,368 | B2 | 7/2008 | Arnouse |
| 7,855,654 | B2 | 12/2010 | Katz |
| 7,948,401 | B2 | 5/2011 | Wartofsky et al. |
| 8,538,603 | B2 | 9/2013 | O'Connor et al. |
| 8,687,375 | B2 | 4/2014 | Uy et al. |
| 8,727,263 | B2 | 5/2014 | Fabre et al. |
| 8,766,820 | B2 | 7/2014 | Santiago Fontaina |
| 9,403,602 | B1 | 8/2016 | Heinrich et al. |
| 9,540,112 | B2 | 1/2017 | Cavan et al. |
| 9,602,187 | B2 | 3/2017 | Jacobs et al. |
| 9,613,543 | B2 | 4/2017 | Whitlow et al. |
| 9,919,712 | B1 | 3/2018 | Doyen et al. |
| 2002/0173888 | A1 | 11/2002 | Shelton et al. |
| 2003/0056491 | A1 | 3/2003 | Coleman et al. |
| 2004/0225474 | A1 | 11/2004 | Goldfine et al. |
| 2009/0069707 | A1 | 3/2009 | Sandford |
| 2010/0271198 | A1 | 10/2010 | Boling et al. |
| 2011/0122019 | A1 | 5/2011 | Lee et al. |
| 2012/0007750 | A1 | 1/2012 | Gorabi et al. |
| 2015/0134154 | A1 | 5/2015 | Colin |
| 2015/0213634 | A1* | 7/2015 | Karmarkar ............. A61B 5/163 345/589 |
| 2016/0047880 | A1 | 2/2016 | Helfrick |
| 2016/0236790 | A1 | 8/2016 | Knapp et al. |
| 2017/0082455 | A1 | 3/2017 | Adler et al. |
| 2017/0083757 | A1 | 3/2017 | Enomoto et al. |
| 2017/0106997 | A1 | 4/2017 | Bekanich |
| 2017/0132943 | A1 | 5/2017 | Moon et al. |
| 2017/0248676 | A1 | 8/2017 | Murphy et al. |
| 2017/0248701 | A1 | 8/2017 | Adler et al. |
| 2017/0303842 | A1 | 10/2017 | Yoshida et al. |
| 2017/0334456 | A1* | 11/2017 | Deligianni ........ B60W 50/0098 |
| 2018/0126999 | A1* | 5/2018 | Selvaraj ................ B60W 40/08 |
| 2018/0299530 | A1 | 10/2018 | Polynin et al. |
| 2018/0364706 | A1 | 12/2018 | Schwindt |
| 2019/0213892 | A1 | 7/2019 | Schwindt |

FOREIGN PATENT DOCUMENTS

| | | |
|---|---|---|
| EP | 2434465 A2 | 3/2012 |
| GB | 2491984 A | 12/2012 |
| GB | 2534678 A | 8/2016 |
| JP | 2007/122579 A | 5/2007 |
| KR | 20070117518 A | 12/2007 |
| KR | 20130059162 A | 6/2013 |
| WO | WO2011/012156 A1 | 2/2011 |
| WO | WO2014/053762 A1 | 4/2014 |
| WO | WO2018/158621 A1 | 9/2018 |

OTHER PUBLICATIONS

European Search Report Corresponding to Application No. 19214621 dated May 11, 2020.
HOF. Global Aeronautical Distress and Safety System (GADSS). ICAO GADSS Advisory Group. Version 6.0, Jul. 6, 2017, 52 pages.
HOF, Adhoc Working Group on Aircraft Tracking—Revised Report, ICAO, Jun. 12, 2015.
Pichavant, Aircraft Tracking and Flight Data Recovery, The Aircraft Manufacturer View, Apr. 2016, 32 pages.

* cited by examiner

METHOD OF ASSESSING A PILOT EMOTIONAL STATE

PRIORITY INFORMATION

The present application claims priority to GB 1820115.2 filed on Dec. 11, 2018.

BACKGROUND

Contemporary aircraft travel flight paths that generally includes a climb, a cruise, and a descent. Pilots along with flight management systems (FMS) implement the flight plan. The FMS may generate the flight plan by taking into account parameters specific to the aircraft and to the flight conditions such as the payload, the weight of the aircraft, the quantity of fuel onboard, temperature, wind, altitude, etc., and of the time constraints imposed by the air traffic control. The flight plan may describe all the waypoints or positions through which the aircraft is to pass, with the altitude and corresponding speed at each waypoint.

Pilot emotion state can vary before takeoff or during the course of any flight. If real-time data of a pilot is indicative of an emotional state outside baseline pilot parameters, it can be beneficial to alert a ground crew to the pilot's emotional state. For example, if real-time pilot data shows a sudden spike or drop in pulse rate, this might be indicative of a pilot medical condition, to which the system might alert emergency medical personnel. In another example, if real-time pilot data before flight shows a pilot is angry or stressed beyond a normal pilot baseline model, it might be beneficial to alert a ground crew.

BRIEF DESCRIPTION

In one aspect, the disclosure relates to a method of assessing a pilot emotional state and sending an alert based on the emotional state. The method includes tracking during a time period, using at least one sensor, one of an image sensor data, voice data or a biometric parameter of a pilot. Determining, using a controller that is operatively connected to at least one sensor, a probability of a likely emotional state from a list of emotional states of a pilot based on one of the image sensor data, voice data or the biometric parameter. Comparing, using a processor, the probability of one of the likely emotional states of the pilot with a baseline emotional state of the pilot. Sending, using the controller, an alert if most likely emotional state deviates from the baseline emotional state by a predetermined threshold.

In another aspect, the disclosure relates to a method of adjusting a flight crew before a planned flight. The method includes tracking over a time period, using at least one sensor, image sensor data, voice data or a biometric parameter of a pilot over one or more flights of an aircraft before the planned flight. Determining during the one or more flights, using a controller that is operatively connected to the at least one sensor, a probability for each likely emotional state from a list of emotional states of a pilot based on one of the image sensor data, voice data or the biometric parameter. Comparing, using a processor, the probability of one of the likely emotional states of the pilot with a baseline model emotional state of the pilot. Determining if the emotional state of the pilot varies based on the flight crew. Adjusting, using the controller, the crew roster prior to the planned flight if the emotional state of the pilot is one of stress or anger when working with a specific flight crew.

DETAILED DESCRIPTION

Figure 1:
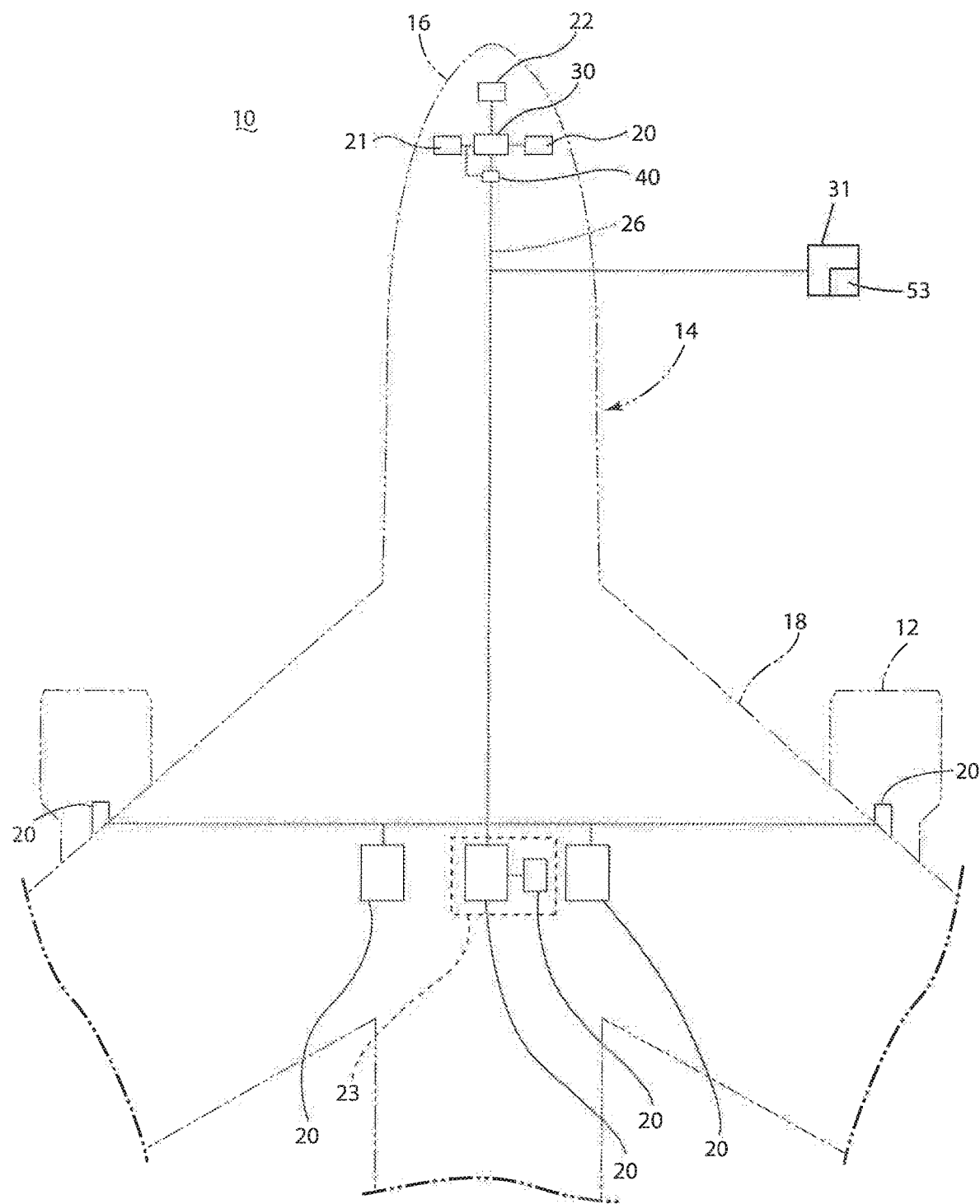
FIG. 1 is a top-down schematic view of a portion of an aircraft according to various aspects described herein.

Aspects of the present disclosure are directed to a method of assessing a pilot emotional state and sending an alert if the emotional state falls outside a predetermined threshold. As used herein, emotional state means a pilot's current physical condition or behavior that is indicative a pilot's current state of mind. Prior to or during operation of an aircraft, it can be important to understand the emotional state of a pilot to understand if the pilot is stressed, angry, happy, relaxed, intoxicated, having a medical issue, etc. If a pilot is stressed, angry, intoxicated, or having a medical issue it may be beneficial to remove the pilot from service of the aircraft or in some cases alert medical personnel.

Every time a pilot enters a cockpit, data indicative of a pilot's emotional state can be collected. During a pre-flight routine, a pilot's voice, body movements, eye movements and various biometric parameters such as heart rate and blood pressure can be monitored and stored as data. Baseline statistics can be stored that are indicative of pilot's emotional or behavioral state. These statistics can used as a comparison for understanding a pilot's current emotional state. For example, if real-time data of a pilot is indicative of anger, i.e. loud voice, darting eye movements, high pulse rate, the system might alert a ground crew to the pilot's emotional state. In another example, if the real-time data shows a sudden spike or drop in pulse rate, this might be indicative of a pilot medical condition, to which the system might alert emergency medical personal. In these cases, it might be beneficial to remove the pilot from service of the aircraft.

It should be recognized that pilot stress levels and behaviors can be function of the pilot's personal habits such as food intake, exercise, and even sleep habits. Baseline models of pilot's ordinary or typical emotional state can be developed to provide a threshold indictor of the pilot baseline emotional state characteristics. The pilot's emotional state can vary over time or even flight-to-flight. For example, if a pilot did not get much rest before a flight, the pilot might become stressed or angry more easily. In other words, fatigue might increase stress or anger sensitivity to workload and minor changes in pilot environment can have a larger detrimental impact. As a result, it can be beneficial to track a pilot's emotional state during flight and adjust the pilot's workload when the pilot's emotional state exceeds a predetermined threshold.

For purposes of illustration, the present disclosure will be described in the context of a flight management system in an aircraft environment. It will be understood, however, that the disclosure is not so limited and may have general applicability in non-aircraft applications, such as other mobile applications including rail or ship transportation.

As used herein, "a set" can include any number of the respectively described elements, including only one element. All directional references (e.g., radial, axial, proximal, distal, upper, lower, upward, downward, left, right, lateral, front, back, top, bottom, above, below, vertical, horizontal, clockwise, counterclockwise, upstream, downstream, forward, aft, etc.) are only used for identification purposes to aid the reader's understanding of the present disclosure, and do not create limitations, particularly as to the position, orientation, or use of the disclosure. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order, and relative sizes reflected in the drawings attached hereto can vary.

As used herein, a "controller" can include at least one processor and memory. Non-limiting examples of the memory can include Random Access Memory (RAM), Read-Only Memory (ROM), flash memory, or one or more different types of portable electronic memory, such as discs, DVDs, CD-ROMs, etc., or any suitable combination of these types of memory. The processor can be configured to run any suitable programs or executable instructions designed to carry out various methods, functionality, processing tasks, calculations, or the like, to enable or achieve the technical operations or operations described herein. The program can include a computer program product that can include machine-readable media for carrying or having machine-executable instructions or data structures stored thereon. Such machine-readable media can be any available media, which can be accessed by a general purpose or special purpose computer or other machine with a processor. Generally, such a computer program can include routines, programs, objects, components, data structures, algorithms, etc., that have the technical effect of performing particular tasks or implement particular abstract data types.

FIG. 1 schematically illustrates an aircraft 10 according to various aspects described herein. One or more propulsion engines 12 can be coupled to a fuselage 14, a cockpit 16 can be positioned in the fuselage 14, and wing assemblies 18 can extend outward from the fuselage 14. A plurality of aircraft systems 20 that enable proper operation of the aircraft 10 can be included as well as a flight control computer 22 (or "computer" 22). While a commercial aircraft has been illustrated, it is contemplated that aspects of the disclosure can be used in any type of legacy aircraft, for example, without limitation, fixed-wing, rotating-wing, rocket, or personal aircraft.

The plurality of aircraft systems 20 can reside within the cockpit 16, within an electronics and equipment bay 23, or in other locations throughout the aircraft 10 including that they can be associated with the engines 12. Such aircraft systems 20 can include but are not limited to: an electrical system, an oxygen system, hydraulics and/or pneumatics system, a fuel system, a propulsion system, navigation systems, flight controls, audio/video systems, an Integrated Vehicle Health Management (IVHM) system, and systems associated with the mechanical structure of the aircraft 10. A variety of aircraft systems 20 have been illustrated for exemplary purposes and it will be understood that they are only a few of the systems that can be included in the aircraft 10.

A data network 26 over which the plurality of aircraft systems 20 can communicate with each other and provide information to a crew of the aircraft 10 can be included. For example, the aircraft systems 20 can output various information to a flight deck 30 located in a cockpit 16 of the aircraft 10.

A communication interface 40 can be located within the aircraft 10 and operably coupled to at least some of the plurality of aircraft systems 20. The communication interface 40 has been illustrated as being included in the cockpit 16. It is contemplated that the communication interface 40 can be located in other locations within the aircraft 10 including within the electronics and equipment bay 23. Although only one communication interface 40 has been illustrated, it is contemplated that the aircraft 10 can have multiple communication interfaces. The communication interface 40 can be utilized for communication with other aircraft or a ground station 31, such as by radio contact in a non-limiting example. In addition, the communication interface 40 can transmit or receive data, including audio or visual data as appropriate.

The ground station 31 can be in communication with the data network 26 or communication interface 40. The ground station 31 can have a processor and software and capabilities for uploading or downloading software or data to the aircraft. The ground station 31 might also capability to store, analyze, and manipulate flight data with data analysis or other statistical software. It should be recognized that the aircraft 10 might also have a computing system capable of storing, analyzing, and manipulating flight data with data analysis or other statistical software.

Figure 2:
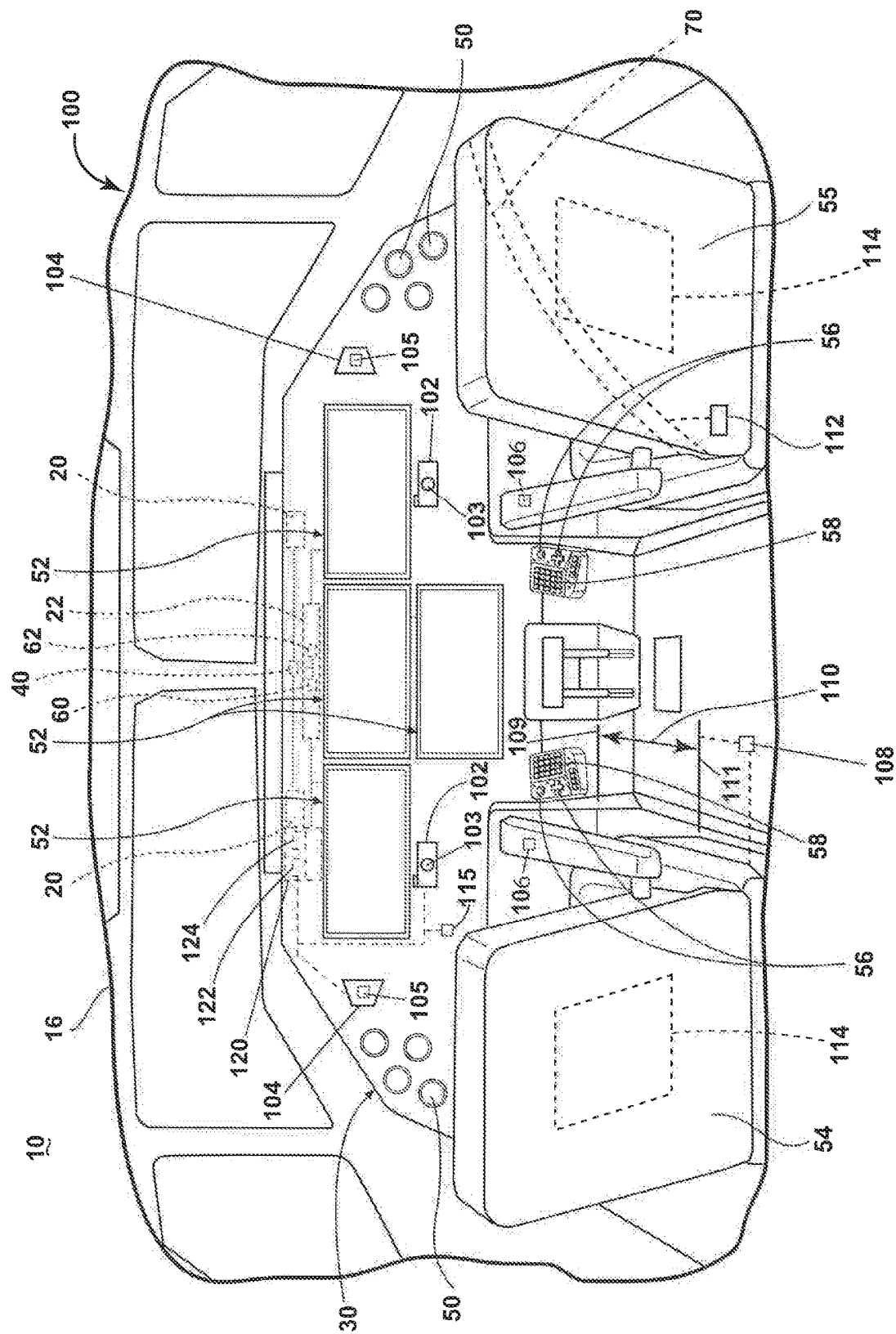
FIG. 2 is a perspective view of a cockpit of the aircraft of FIG. 1 including an attention tracking system according to various aspects described herein.

FIG. 2 illustrates a portion of the cockpit 16 of the aircraft 10 and an exemplary flight deck 30 having various instruments 50 and flight displays 52. A first pilot (herein, a "pilot") can be present in a seat 54 at the left side of the cockpit 16 and a second pilot (herein, a "co-pilot") can be present at the right side of the cockpit 16 in a seat 55 and the flight deck 30 can be located in front of the pilot and co-pilot and can provide the flight crew with information to aid in operating the aircraft 10. The flight displays 52 can include either primary flight displays or multi-function displays and can display a wide range of aircraft, flight, navigation, and other information used in the operation and control of the aircraft 10. Further, both the various instruments 50 and flight displays 52 of the flight deck 30 can provide one or more visual indicia indicative of a corresponding health condition of one or more of the aircraft systems 20.

The instruments 50 and flight displays 52 can be laid out in any manner including having fewer or more instruments or displays. Further, the flight displays 52 need not be coplanar and need not be the same size. A touch screen display or touch screen surface can be included in the flight display 52 and may be used by one or more flight crew members, including the pilot and co-pilot, to interact with the systems of the aircraft 10. Such touch screen surface can take any suitable form including that of a liquid crystal display (LCD) and can use various physical or electrical attributes to sense inputs from the flight crew. It is contemplated that the flight display 52 can be dynamic and that one or more cursor control devices 56 and/or one or more multifunction keyboards 58 can be included in the cockpit 16 and can be used by one or more flight crew members to interact with the systems of the aircraft 10. In this manner, the flight deck 30 can be considered a user interface for the aircraft systems 20 and the aircraft 10.

The flight control computer 22 can be operably coupled to components of the aircraft 10 including the aircraft systems 20, instruments 50, flight displays 52, touch screen surfaces, cursor control devices 56, keyboards 58, etc. The flight control computer 22 can receive inputs from any number of aircraft systems 20 or software programs responsible for managing the acquisition and storage of data. The flight control computer 22 can also be in the form of a controller, and can be connected with other controllers of the aircraft 10. The flight control computer 22 can include memory 60 and processing units 62, which can be running any suitable programs to implement a graphical user interface (GUI) and operating system. The flight control computer 22 can include or be associated with, any suitable number of individual microprocessors, power supplies, storage devices, interface cards, auto flight systems, flight management computers, and other standard components. The flight control computer 22 can include or cooperate with any number of software programs (e.g., flight management programs) or instructions designed to carry out the various methods, process tasks, calculations, and control/display functions necessary for operation of the aircraft 10.

The communication interface 40 can be communicably coupled to the flight control computer 22 or other processors of the aircraft 10 as well as any number of the plurality of aircraft systems 20 to transfer information on and off the aircraft 10. The communication interface 40 can include any desired communication mechanism capable of wirelessly linking with other systems and devices, such as by radio contact in a non-limiting example. For example, one of the aircraft systems 20 can be in the form of a distress tracker 21 configured to transmit a state of aircraft distress (for example, "normal," "abnormal," or "distressed").

A pilot tracking system or tracking system 100 is illustrated as being in communication with the flight control computer 22. It will be understood that the tracking system 100 can be hard wired to the flight control computer 22 or can communicate in any suitable manner with the flight control computer 22 including via wireless communication. Alternatively, the tracking system 100 can be included as a module within the flight control computer 22.

The tracking system 100 can include at least one imaging module 102 and at least one audio module 104. The imaging module 102 can include an image sensor 103 configured to sense visual information about a pilot or co-pilot, such as rapid eye movement, eyes moving one direction or another, being open or closed, a direction of gaze, or a facial state such as eyebrows raised or lowered, by way of non-limiting examples and provide an output signal based thereon. In addition, the image sensor 103 can be configured to capture or sense images beyond the human visible spectrum such as in the infrared, ultraviolet, electromagnetic or other range. An eye movement or body movement parameter can be stored by the tracking system 100 The imaging module 102 or the flight control computer 22 can also be in signal communication with any of the flight displays 52, such as to display a visual indication based on the sensed visual information from the imaging module 102.

The audio module 104 can include an audio sensor 105 configured to sense audio information about a pilot or co-pilot, such as a language being spoken in the cockpit 16, a voice volume, tone, slurred or altered speech, a speech pattern, or sounds that can occur due to pilot or co-pilot interaction with an aircraft system 20 such as striking the flight deck 30 or typing on the multifunction keyboard 58 and provide an output signal based thereon. In other words, the audio module 104 can be configured to use voice recognition and language analysis to help sense a pilot's emotional state. The audio module 104 can also provide audio feedback or sound to the pilot or co-pilot, such as through speakers mounted within the cockpit or through headphones worn by the pilot or co-pilot. Further, the audio module 104 can be in signal communication with the imaging module 102. For example, the imaging module 102 can provide an indication for transmission through the audio module 104, such as spoken commands in a low-visibility environment within the cockpit 16. The audio module 104 can also provide a signal for transmission via the imaging module 102, such as a flashing light display or text-based indicator to be read by a pilot or co-pilot.

At least one biometric sensor 106 configured to sense a biometric parameter of the pilot or co-pilot can be included in the tracking system 100. For example, a biometric sensor 106 positioned on the first seat 54 can be configured to sense or detect a heart rate, breathing rate, perspiration rate, or bodily motion of the pilot when the pilot is sitting in the first seat 54. Alternatively, the biometric sensor 106 can be positioned on a wearable device such as a wrist strap or headband. In still another example, the biometric sensor 106 can be in the form of an optical sensor, e.g. a camera that monitors the pilot or co-pilot.

In addition, a seat tracking module 108 can control a seat distance 110 between the first seat 54 and the flight deck 30. While not shown, the second seat 55 can also include such a seat tracking module 108. Further, a seat belt sensor 112 can sense the position of a seat belt 70 on the first seat 54 or the second seat 55, such as the seat belt 70 being buckled or unbuckled.

A haptic feedback generator 114 can be coupled or integrated with either or both of the first and second seats 54, 55. The haptic feedback generator 114 can be configured to vibrate, such as a steady or varying vibration pattern, to provide feedback to the pilot or co-pilot. In a non-limiting example wherein the aircraft 10 is not level during flight in low-visibility conditions, the haptic feedback generator 114 can vibrate on a right-hand portion or left-hand portion of the seat 54, 55 to indicate to a pilot or co-pilot which direction to bank the aircraft 10 for correct orientation when flying.

A timer 115 can also be included in the tracking system 100 and is illustrated as being coupled to the flight deck 30. The timer 115 can be positioned anywhere within or outside of the cockpit 16. The timer 115 can be configured to track an elapsed time of an event or to provide an alarm or other indication at a predetermined time. Non-limiting examples where the timer 115 can be utilized include tracking an elapsed time of flight, an elapsed time of a pilot interaction with an aircraft system 20 (such as updating flight records via the multifunction keyboard 58), tracking an elapsed sleep time, indicating a time for changing a flight direction, or indicating a wake time.

An additional controller 120 having a processor 122 and a memory 124 can also be included in the tracking system 100. The controller 120 is illustrated as being coupled to the flight deck 30 and in signal communication with any or all of the flight control computer 22, instruments 50, flight displays 52, memory 60, processing unit 62, imaging module 102, audio module 104, biometric sensor 106, seat tracking module 108, seat belt sensor 112, haptic feedback generator 114, or timer 115. Dashed lines have been used to illustrate a portion of the signal connection between the above-described components. The lack of a dashed line for signal connections is done for clarity of the figures, and it will be understood that components not connected by a dashed line can nonetheless be in signal communication.

Figure 3:
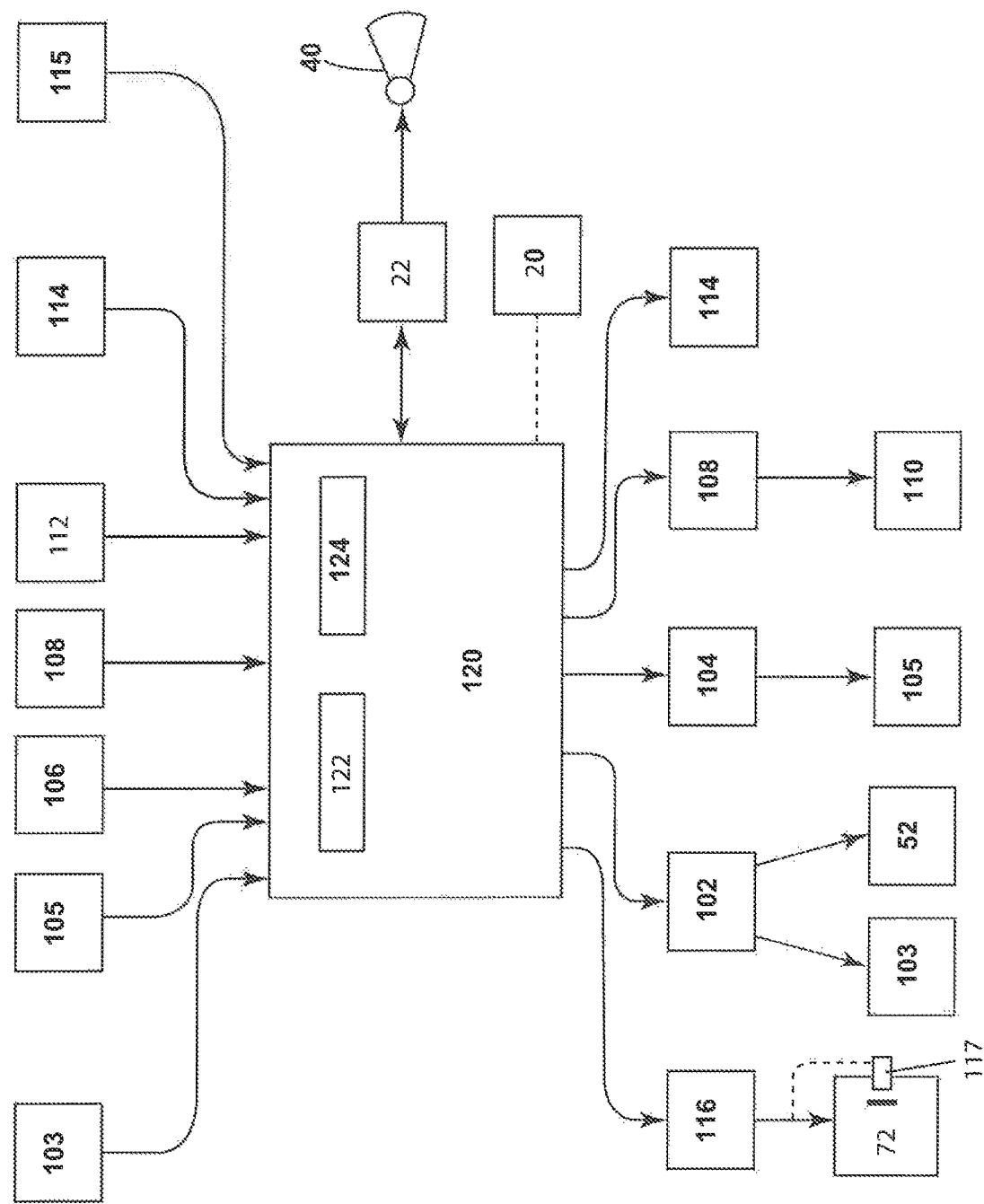
FIG. 3 is a schematic illustration of the attention tracking system of FIG. 2 according to various aspects described herein.

FIG. 3 schematically illustrates components of the tracking system 100 in exemplary communicative connection, where a separate controller 120 is shown in signal connection with the various modules and sensors described above. Alternatively, it will be understood that the flight control computer 22 can be utilized or that each module or any combination of modules can include their own controller, processor, or memory. Arrows have been included to indicate an exemplary signal or control direction, and are provided for clarity in discussion. It will be understood that any signal communication or control between connected components in FIG. 3 can be transmitted in either direction, and an arrow's illustrated direction does not imply a one-way signal or control direction.

A door lock module 116 with a door lock sensor 117 can further be included in the tracking system 100. For example, a cockpit door 72 can include the door lock module 116 configured to sense whether the door 72 is locked or unlock. The module 116 can also automatically lock or unlock the door 72 based on a control signal within the tracking system 100.

The controller 120 can be operably connected to and receive input from any or all of the flight control computer 22, image sensor 103, audio sensor 105, biometric sensor 106, seat tracking module 108, seat belt sensor 112, haptic feedback generator 114, timer 115, or door lock module 116. Any of the inputs received by the controller 120 can be stored in the memory 124. For example, the memory 124 can store a history of audio input or recordings from data gathered within the cockpit 16, or an elapsed time since a pilot last interacted with a flight display 52 (FIG. 2).

The processor 122 of the controller 120 can send a signal or control command to any or all of the imaging module 102, audio module 104, seat tracking module 108, haptic feedback generator 114, or door lock module 116. In another non-limiting example, the processor 122 can send a signal to the imaging module 102, such as a visual message to be read by the pilot or co-pilot on the flight display 52, or a command to enable or disable the image sensor 103.

It is further contemplated that the controller 120 of the tracking system 100 can issue a signal or command to another aircraft system, such as the communication interface 40 via the flight control computer 22. In such a case, the controller 120 can communicate with an external aircraft or ground station (not shown). The controller 120 can also be communicatively coupled with any other aircraft system 20 as desired.

Figure 4:
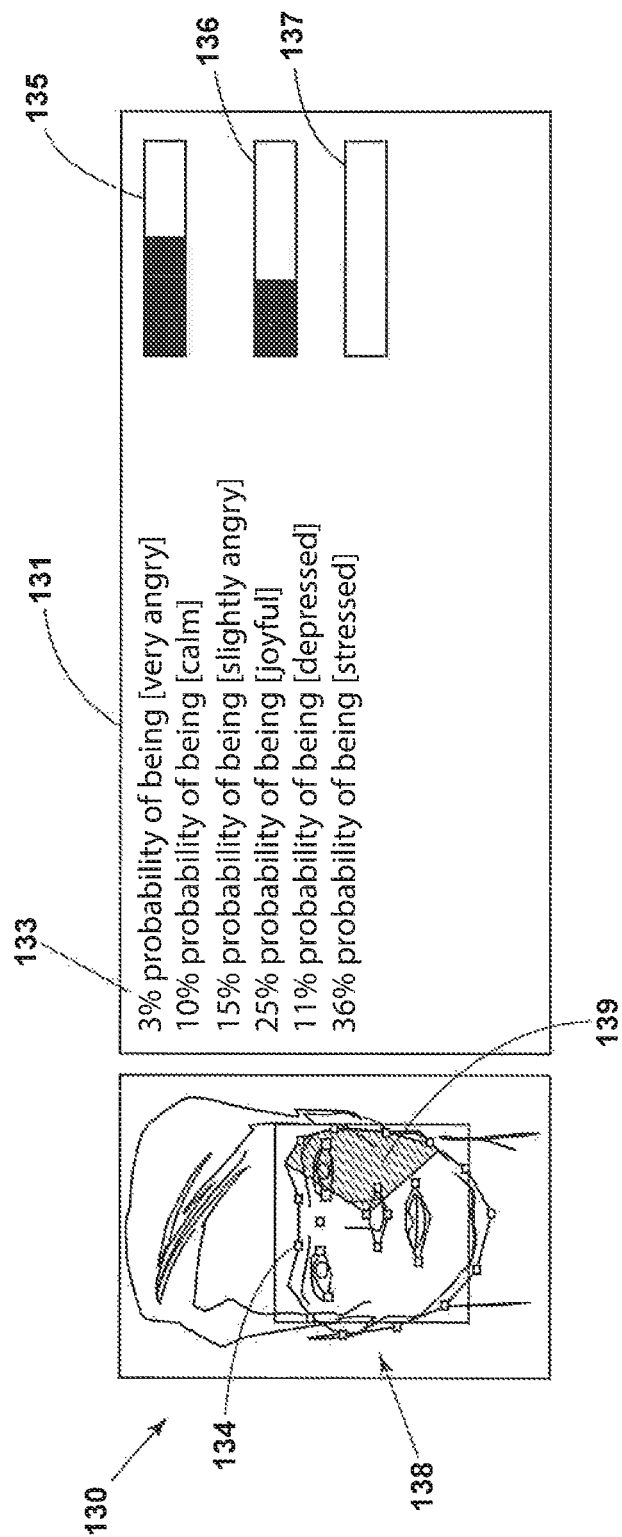
FIG. 4 is a graphic of a pilot facial recognition in accordance with the tracking systems of FIG. 2.

FIG. 4 is an illustration of a captured image 130 of a pilot from image sensor 103 and illustrates one exemplary way of assessing a pilot's emotional state. In this illustration, the image sensor 103 can capture the facial expression 138 of the pilot at a particular point in time. The facial expression 138 can be analyzed by facial recognition software 53 for determining a likely emotional state of the pilot. The facial expression software 53 can capture one or more data points 134, or data points covering areas 139, of the pilot facial expression 138 and analyze one or more characteristics of the pilot face including pilot mouth, right eye, or left eye being opened or closed. These can be captured and displayed as bar graphs representative of pilot open mouth 135, pilot right eye closed 136 or pilot left eye closed 137. It should be recognized that other facial data points and characteristics can be captured and analyzed.

In one example, the facial recognition software 53 can be programmed to calculate a probability 133 of likely emotional states 132 such as very angry, angry, slightly angry, joyful, depressed, stressed, etc. from an image 130 captured by the image sensor 103. The facial recognition software 53 can analyze the data points 134, or data areas 139, for facial characteristics such as pilot mouth, right eye, or left eye being opened or closed. The data can be stored and analyzed to determine a pilot emotional state 131. The facial recognition software 53 can be stored on the ground station 31, in the flight management computer 22, or in a separate processing unit.

For purposes of the exemplary embodiment, the facial recognition software 53 is in communication with the controller 120 and image sensor 103. The facial recognition software 53 can enable the controller 120 to assign a probability 133 to each emotional state 131 based on analysis from the facial recognition software 53. As illustrated, the controller 120 can assign a probability 133 to each emotional state 131 such that the sum of the probabilities for each emotional state equals 100%. In another example, the controller 120 can assign a probability 133 to each emotional state 131 such that the probability for each emotional state ranges from 0-100%. In either case, once the probabilities 133 are assigned, the controller 120 can assess the pilot's emotional state as the highest-probability from the listed emotional states. In other words, in the illustrated example, the controller 120 will identify "stressed" as the pilot's emotional state at that moment in time.

Since the captured image 130 is indicative of only a single moment in time, the tracking system 100 can repeatedly capture and analyse this data over any period of time to identify a pilot's likely emotional state over the period of time. In one example, the tracking system 100 can capture numerous images from image sensor 103 and average data, identify trends, or use other statistical analysis to identify the probability of the pilot's emotional state. Moreover, the tracking system 100 can correlate the captured image 103 with other collected data such as pilot voice data or a biometric parameter to help assess the pilot's emotional state. If voice data, biometric parameters, and image capture data each indicate a likely emotional state, then the controller 120 can determine the pilot's emotional state and, if necessary, can be programmed to alert either a ground crew or medical personnel of the pilot's emotional state. While use of voice data and biometric parameters can increase the likelihood of accurately assessing a pilot's emotional state, such data is not required.

Figure 5:
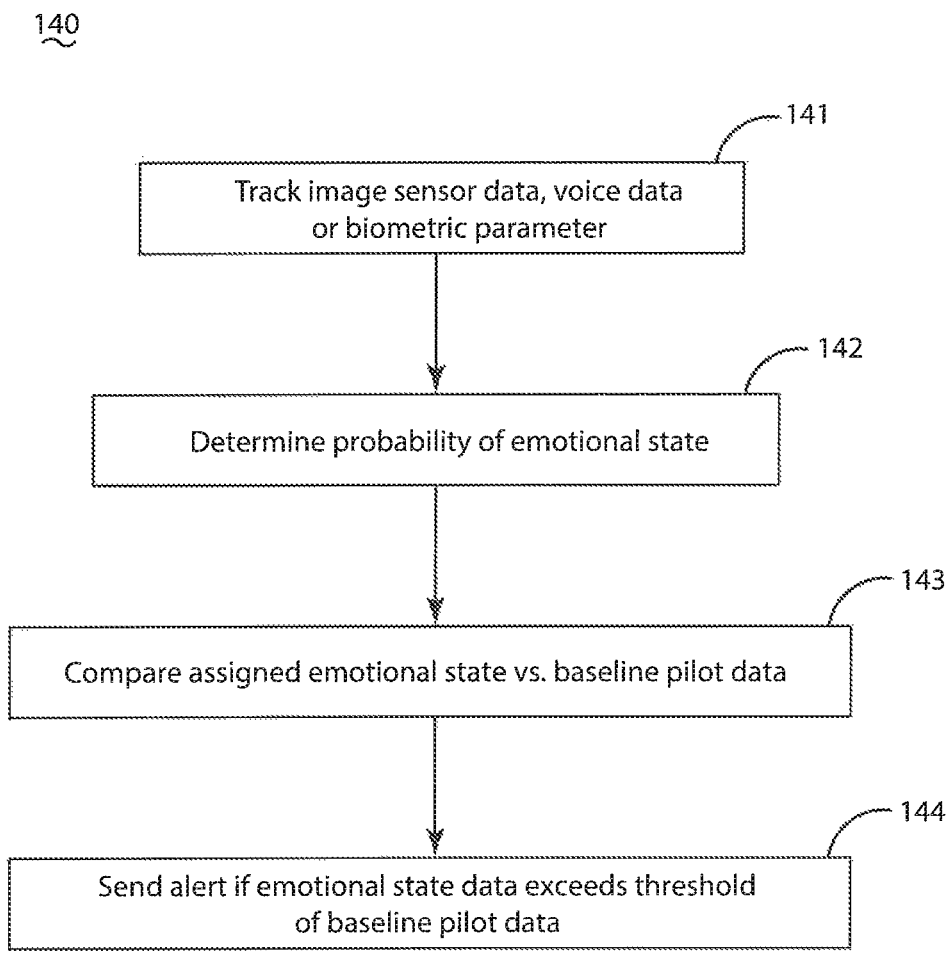
FIG. 5 is a flowchart illustrating a method of assessing a pilot emotional state for an aircraft of FIG. 1 and sending an alert based on the emotional state according to various aspects described herein.

Referring now to FIG. 5, a method 140 of assessing a pilot emotional state is illustrated. The method 140 begins at 141 with tracking image sensor 103 data, voice data, or a biometric parameter of the pilot to determine an emotional state of the pilot either before or during flight of the aircraft 10 by using at least one sensor within the tracking system 100. The tracking of image sensor data, voice data or biometric parameters can occur over any period of time that the pilot is on-board such as preflight or over an entire flight, or portions of a flight.

The image sensor 103 can track both the eye movements and body movements of the pilot preflight or during all or portions of the flight. For example as described with respect to FIG. 4, the image sensor 103 can capture one or more facial expressions 138 of the pilot, and the controller 120 in combination with facial recognition software 53 can determine an emotional state of the pilot. The image sensor 103 can capture open, closed, darting, rapidly moving eyes or can visually detect the pilot's hand interacting with the keyboard 58 or flight display 52. In an example where the flight display 52 includes a touchscreen, the controller 120 can detect that the pilot has touched or interacted with the touchscreen flight display 52. The image sensor 103 can capture rapid or forceful body movements with respect to flight display, and such data can be used to correlate with a pilot's emotional state.

Audio sensor 105 data can capture voice data of the pilot. Biometric parameters of the pilot can also be tracked such as heart rate, breathing rate, skin temperature, and the like. The audio sensor 105 data and biometric parameters can be indicative of whether a pilot is angry, calm, stressed or have some other emotional state. It should be recognized that this data can be used to make real-time decisions about the pilot's emotional state pre-flight or during a flight or the data can be saved to a database and processed after the flight. The data can also be added to or integrated with other pilot data to establish baseline statistics of the pilot.

At 142, the controller 120 can determine a probability for each likely emotional state from a list of emotional states of a pilot based on one of the image sensor data, voice data or the biometric parameter. At this step, the controller 120 can assign a probability 133 to each emotional state 131 based on analysis from the facial recognition software. As discussed, the controller 120 can assign a probability 133 to each emotional state 131 such that the sum of the probabilities for each emotional state equals 100% or can assign a probability 133 to each emotional state 131 such that the probability for each emotional state ranges from 0-100%. In either case, once the probabilities 133 are assigned, the controller 120 can assess the pilot's emotional state as the highest-probability.

At 143, the controller 120 can compare the assigned emotional state to baseline data of the pilot, representative of the pilot's typical or previous emotional states. The baseline data simply gives the controller 120 data to compare against to determine whether any of the real-time pilot data deviates beyond a predetermined threshold of the baseline data. It should be recognized that baseline pilot data can be collected or generated over time as the pilot flies various flights. Data can be collected, analysed and stored and a baseline pilot profile can be generated. The pilot profile can be updated after each flight, so every time the pilot flies the real-time emotional state of the pilot can compared with the baseline data.

At 144, the controller 120 can send an alert to one of a ground station or medical personal if the real-time pilot emotional state data deviates beyond a predetermined threshold of the baseline data. For example, if a pilot's real-time emotional state is determined to be very angry, the controller 120 might send an alert to the ground station 31 to alert appropriate people. Ground station personnel might choose to intervene or interview the pilot before the flight takes off.

Figure 6:
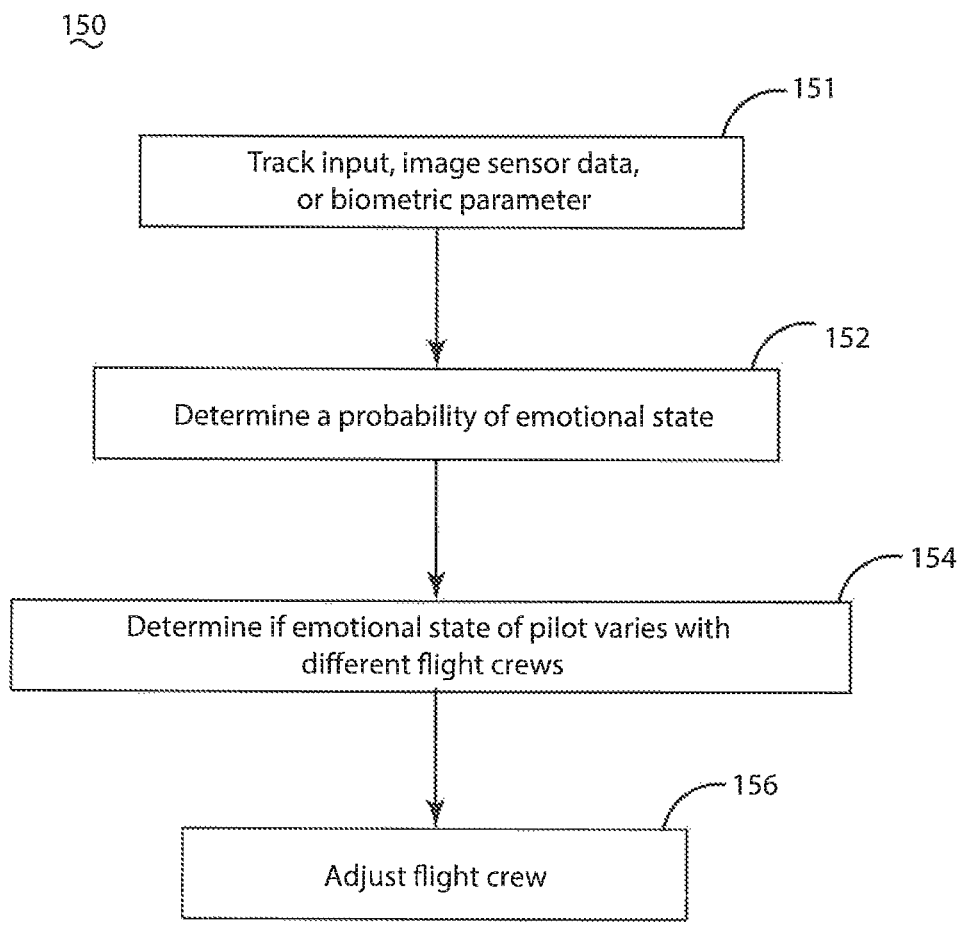
FIG. 6 is a flowchart illustrating another method of adjusting a flight crew before a planned flight for an aircraft of FIG. 1 according to various aspects described herein.

Turning to FIG. 6, a method 150 of adjusting a flight crew based on an emotional state of a pilot is illustrated. The method 150 begins at 151 with tracking over a time period, image sensor data, voice data or a biometric parameter of a pilot over one or more flights of an aircraft before the planned flight using at least one sensor within the tracking system 100. The tracking of image sensor data, voice data or biometric parameters can occur over any period of time that the pilot is on-board such as preflight or over an entire flight, or portions of a flight. To the extent multiple pilots are on board, the method 150 would include tracking image sensor data, voice data or biometric parameters for each of the pilots.

As previously discussed, the image sensor 103 can track both the eye movements and body movements of the each of the pilots pre-flight or during all or portions of the flight. Audio sensor 105 data can capture voice data of each of the pilots. Biometric parameters of each of the pilots can also be tracked such as heart rate, breathing rate, skin temperature, and the like. The audio sensor 105 data and biometric parameters can be indicative of whether a pilot is angry, calm, stressed or some other emotional state. It should be recognized that this data can be used to make real-time decisions about the pilot's emotional state pre-flight or during a flight or the data can be saved to a database and processed after the flight. The data can also be added to or integrated with other pilot data to establish a baseline model of the pilot.

At this step, it is also contemplated that data can be tracked and collected from multiple flights over various time frames. The data can be tracked, collected, and analyzed to understand a pilot's emotional state during various time frames pre-flight or during a flight. If multiple pilots are on board, or flight crews work together frequently, data can be tracked and compared to understand if there is tension or stress among pilots and/or crew. Data might reveal that a pilot has higher stress levels when performing with one crew or another. In addition, the data can be categorized and sorted by time frame to create baseline statistics for the pilot. For example, one would expect a pilot to have higher workloads and stress levels during take-off and landing than during cruise or pre-flight. Baseline models of a pilot's typical emotional state can be created during each flight phase and in relation to each flight crew. As should be recognized, the analysis and development of the baseline models can be done on or off aircraft 10 and the pilot profile can be updated after each flight.

At 152, the controller 120 can determine a probability for each likely emotional state from a list of emotional states of a pilot based on one of the image sensor data, voice data or the biometric parameter. The controller 120 performs this step during flights to collect data on each of the multiple pilots. At this step, the controller 120 can assign a probability 133 to each emotional state 131 based on analysis from the facial recognition software. As discussed, the controller 120 can assign a probability 133 to each emotional state 131 such that the sum of the probabilities for each emotional state equals 100% or can assign a probability 133 to each emotional state 131 such that the probability for each emotional state ranges from 0-100%. In either case, once the probabilities 133 are assigned, the controller 120 can assess the pilot's emotional state as the highest-probability.

In other words, at this step 152, for any given flight, data representing a pilot's emotional state can be collected and correlated over distinct periods of time and with respect to various flight crews. In this example, the timer 115 can track the time of flight which can be correlated with the collected pilot data across all or a portion of the flight. Data from each recorded flight can be stored onboard or can be transmitted offsite to a ground station 31 for analysis and processing. This data can be used to create a baseline model for a pilot.

At 154, the controller 120 or other processor can determine if the emotional state of the pilot varies based on the flight crew. In some instances, flight crews might not get along and there might be tension, stress, or anxiety among one or more of the pilots and/or crew. Analysis of data might reveal that a pilot has higher stress levels when performing with one crew or another. Thus, at this step, it is contemplated that the controller 120 assesses that the pilot's most likely emotional state during all or a portion of the flight and compares the pilot emotional state to all or a portion of a flight with a separate crew. If the pilot's emotional state is stress or anger during all or a portion of one flight and calm and relaxed during a portion of another flight, the controller 120 might indicate that the emotional state of the pilot varies between flight crews.

At 156, prior to a planned flight, the controller 120 or other processer that is operatively connected to the flight control computer can adjust the crew roster prior to the planned flight if the emotional state of the pilot is one of stress or anger when working with a specific flight crew.

In this scenario, the controller 120 or other processor can predict when two pilots or crew members in the planned flight will have a tense or stressed working relationship and can adjust the flight crew by removing or reassigning one or more of the crew members. Moreover, the controller 120 or other process can predict when additional or less crew may be required for certain flights or certain conditions.

To the extent not already described, the different features and structures of the various embodiments can be used in combination, or in substitution with each other as desired. That one feature is not illustrated in all of the embodiments is not meant to be construed that it cannot be so illustrated, but is done for brevity of description. Thus, the various features of the different embodiments can be mixed and matched as desired to form new embodiments, whether or not the new embodiments are expressly described. All combinations or permutations of features described herein are covered by this disclosure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of adjusting a flight crew before a planned flight, the method comprising:
   tracking over a time period, using at least one sensor, image sensor data, voice data or a biometric parameter of a pilot over one or more flights of an aircraft before the planned flight;
   determining during the one or more flights, using a controller that is operatively connected to at least one sensor, a probability for each of a likely emotional state from a list of emotional states of a pilot based on one of the image sensor data, voice data or the biometric parameter;
   comparing, using a processor, the probability of one of the likely emotional states of the pilot with a baseline model emotional state of the pilot;
   determining if the emotional state of the pilot varies based on the flight crew;
   adjusting, using the controller, the crew roster prior to the planned flight if the emotional state of the pilot is one of stress or anger when working with a specific flight crew.

2. The method of claim 1, wherein a sum of each probability for each emotional state equals 100%.

3. The method of claim 2, further comprising selecting from the probabilities for each emotional state, using the controller, the highest-probability as the pilot's likely emotional state.

4. The method of claim 1, wherein the probability for each emotional state ranges from 0-100%.

5. The method of claim 4, further comprising selecting from the probability for each emotional state, using the controller, the highest-probability as the pilot's likely emotional state.

* * * * *